United States Patent
Bunegin et al.

(10) Patent No.: US 8,685,709 B2
(45) Date of Patent: *Apr. 1, 2014

(54) FLUIDICS BASED PULSATILE PERFUSION PRESERVATION DEVICE AND METHOD

(75) Inventors: Leonid Bunegin, Pipe Creek, TX (US); Edward F. Gelineau, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 420 days.

This patent is subject to a terminal disclaimer.

(21) Appl. No.: 12/890,348

(22) Filed: Sep. 24, 2010

(65) Prior Publication Data

US 2011/0212431 A1    Sep. 1, 2011

Related U.S. Application Data

(60) Provisional application No. 61/245,762, filed on Sep. 25, 2009.

(51) Int. Cl.
*A01N 1/00* (2006.01)
*A01N 1/02* (2006.01)

(52) U.S. Cl.
USPC ....... 435/284.1; 435/1.2; 435/1.1; 435/289.1; 435/304.1

(58) Field of Classification Search
USPC ................. 435/1.1, 1.2, 289.1, 284.1, 304.1
See application file for complete search history.

(56) References Cited

U.S. PATENT DOCUMENTS

| | | |
|---|---|---|
| 5,356,771 A | 10/1994 | O'Dell |
| 5,362,622 A | 11/1994 | O'Dell et al. |
| 5,385,821 A | 1/1995 | O'Dell et al. |
| 5,586,438 A | 12/1996 | Fahy |
| 6,569,615 B1 | 5/2003 | Thatte et al. |
| 6,582,953 B2 | 6/2003 | Brasile |
| 6,642,045 B1 | 11/2003 | Brasile |
| 6,673,594 B1 | 1/2004 | Owen et al. |
| 6,794,182 B2 | 9/2004 | Wolf |
| 6,977,140 B1 | 12/2005 | Owen et al. |
| 7,029,839 B2 | 4/2006 | Toledo-Pereyra et al. |

(Continued)

FOREIGN PATENT DOCUMENTS

| | | |
|---|---|---|
| CN | 101322861 | 12/2008 |
| DE | 19922310 | 11/2000 |

(Continued)

OTHER PUBLICATIONS

Search Report and Written Opinion for PCT Application No. PCT/US2010/050230.

*Primary Examiner* — Nathan Bowers
(74) *Attorney, Agent, or Firm* — Meyertons, Hood, Kivlin, Kowert & Goetzel, P.C.; Eric B. Meyertons

(57) ABSTRACT

In one embodiment, a preservation apparatus is described that includes a storage compartment. The storage compartment is configured to hold an organ or tissue and a preservation fluid. A cover assembly is configured to engage the storage compartment. The cover assembly includes a support element, wherein the support element together with the storage compartment define a storage chamber. The cover assembly also includes a lid and a gas permeable membrane disposed between the lid and the support element. The gas permeable membrane and the support element together define a perfusion chamber configured to hold preservation fluid and an organ or tissue during use.

17 Claims, 10 Drawing Sheets

(56) References Cited

U.S. PATENT DOCUMENTS

| | | |
|---|---|---|
| 7,410,474 B1 | 8/2008 | Friend et al. |
| 7,504,201 B2 | 3/2009 | Taylor et al. |
| 2002/0177117 A1 | 11/2002 | Wolf, Jr. |
| 2004/0058432 A1 | 3/2004 | Owen et al. |
| 2004/0224299 A1 | 11/2004 | Garland et al. |
| 2005/0153271 A1 | 7/2005 | Wenrich |
| 2005/0255442 A1 | 11/2005 | Brassil et al. |
| 2006/0121439 A1 | 6/2006 | Baker |
| 2007/0009881 A1 | 1/2007 | Arzt et al. |
| 2007/0015131 A1 | 1/2007 | Arzt et al. |
| 2007/0184545 A1 | 8/2007 | Plaats et al. |
| 2012/0156763 A1* | 6/2012 | Wikswo et al. ............ 435/287.1 |
| 2012/0309078 A1* | 12/2012 | Anderson et al. .......... 435/284.1 |

FOREIGN PATENT DOCUMENTS

| | | |
|---|---|---|
| DE | 102005048625 | 4/2007 |
| JP | 8169801 | 7/1996 |
| JP | 2008120713 | 5/2008 |
| WO | 0018226 | 4/2000 |
| WO | 2004026031 | 4/2004 |
| WO | 2009020412 | 2/2009 |
| WO | 2009041806 | 4/2009 |

\* cited by examiner

FLUIDICS BASED PULSATILE PERFUSION PRESERVATION DEVICE AND METHOD

PRIORITY CLAIM

This application claims the benefit of U.S. Provisional Application No. 61/245,762 filed on Sep. 25, 2010.

BACKGROUND OF THE INVENTION

1. Field of the Invention

The invention generally relates to a method and apparatus for the preservation of living tissues, particularly organs.

2. Description of the Relevant Art

Although tissue transplantation and implantation have been viable since the 1960's, and have increased in popularity since that time, techniques for preservation of tissue have not become normalized. Initially, simple cold storage was used where the tissue was maintained in a cold, nonperfused preservation fluid. Perfused cold storage and hyperbaric cold perfused storage were subsequently shown experimentally to be superior to simple nonperfused cold storage. Since neither perfused cold storage nor hyperbaric cold perfused storage could be practically applied, nonperfused cold storage continued to be preferred. A disadvantage of nonperfused cold storage, however, is the limited period of viability of the tissue, typically due to significant oxygen decline in the storage medium resulting from the stored tissue's metabolic need for oxygen.

Because of the distance that often separates tissue donors and recipients; the portability of storage devices is of critical importance. In addition, the desire to increase the pool of tissue available for transplantation into any one recipient mandates that the storage time for the tissue be extended beyond that permitted with simple hypothermic storage, thus opening the possibility for a world-wide network of donors and recipients.

Pulsatile perfusion devices have been developed to sustain and extend the viability of extracorporeal living tissue for several hours pending the implant of the tissue. The advantage of pulsatile perfusion is that it mimics the natural state of the tissue by inducing flow through its arterial supply with oxygenated fluid, or perfusate. However, only limited success has been achieved with perfusion of tissue in the atmosphere (i.e., without submersing the perfused tissue in the perfusate). The danger of this method of perfusion is that a pressure gradient may develop across the capillary wall of the tissue, which is proportionate to the output of the perfusion pump. Under hypothermic conditions, perfusion pressures in excess of 20 mm Hg have resulted in capillary damage destroying and compromising the viability of the tissue being preserved.

Hypothermic pulsatile perfusion of tissue during storage can significantly extend storage time to 12-24 hours, without loss of tissue viability, due to reduced tissue metabolic rate and oxygen consumption. For example, cooling to 15 C reduces oxygen consumption of myocardial tissue to one-fifth of the rate at room temperature (e.g., 25 C). However, hypothermia alone is less protective than when it is combined with oxygenated perfusion, in that a continuous supply of oxygen is available in the latter case to support the metabolic oxygen requirements.

Hypothermic perfusion devices have been designed and are known in the art. However, devices that are currently available for hypothermic pulsatile perfusion are typically large, require significant volumes of compressed gas and electrical power, and/or also may necessitate an upright level orientation for operation. Additionally, these devices tend to be very complex, consisting of many intricate parts that must work precisely in concert.

SUMMARY OF THE INVENTION

In one embodiment, a preservation apparatus is described that includes a storage compartment. The storage compartment is configured to hold an organ or tissue and a preservation fluid. A cover assembly is configured to engage the storage compartment. The cover assembly includes a support element, wherein the support element together with the storage compartment define a storage chamber. The cover assembly also includes a lid and a gas permeable membrane disposed between the lid and the support element. The gas permeable membrane and the support element together define a perfusion chamber configured to hold preservation fluid during use.

In one embodiment, at least a portion of the bottom surface of the support element is substantially non-planar. The non-planar bottom surface of the support element contacts preservation fluid present in the storage compartment when the cover assembly engages the storage compartment during use.

In another embodiment, a membrane support is positioned between the support element and the lid. The membrane support includes an outer coupling member and one or more membrane support elements extending from the outer coupling member toward an interior region of the membrane support. The gas permeable membrane is coupled to the membrane support such that the membrane support positions the gas permeable membrane between the support element and the lid. The membrane support elements inhibit contact of the membrane with the lid and the support element during use.

In another embodiment, the support element includes an inlet port configured to engage an organ or tissue. The inlet port includes an inlet valve configured to allow flow of fluid from the perfusion chamber to the organ or tissue during use. The inlet valve is configured to inhibit flow of fluids from the organ or tissue to the perfusion chamber during a pumping stage of the device.

Also described is a system for preserving an organ or tissue that includes a preservation apparatus as described herein and an oxygen containing supply source. The system may be disposed in a case having insulation and cooling sources to maintain the preservation apparatus, and its contents, at a temperature below room temperature.

In an embodiment, a preservation apparatus may be used to preserve an organ or tissue. Preservation fluid is added to a preservation apparatus as described herein. An organ or tissue is coupled to an inlet port of the support element. The organ or tissue is placed into the preservation fluid in the storage compartment by placing the cover assembly onto the storage compartment. An oxygen containing gas is provided to a pumping chamber of the preservation apparatus at a pressure sufficient to displace the membrane such that the perfusion cavity is contracted, forcing at least a portion of the preservation fluid in the perfusion cavity through the inlet port into or around the organ or tissue. The inlet port is configured such that the preservation fluid flows unidirectionally through the inlet port to the organ or tissue. As oxygen containing gas is provided to the pumping chamber, the pressure of the storage chamber is measured. When a pressure of the storage chamber is equal to or greater than a predetermined pressure the supply of oxygen containing gas to the pumping chamber is discontinued. Discontinuing of the supply of oxygen containing gas allows flow of preservation fluid from the storage chamber to the perfusion chamber through the one or more outlet ports.

BRIEF DESCRIPTION OF THE DRAWINGS

Advantages of the present invention will become apparent to those skilled in the art with the benefit of the following detailed description of embodiments and upon reference to the accompanying drawings in which.

Figure 1A:
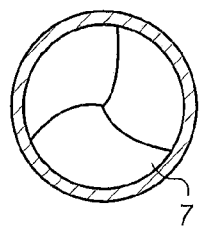
FIG. 1A depicts an embodiment of a tricuspid valve.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

Figure 1B:
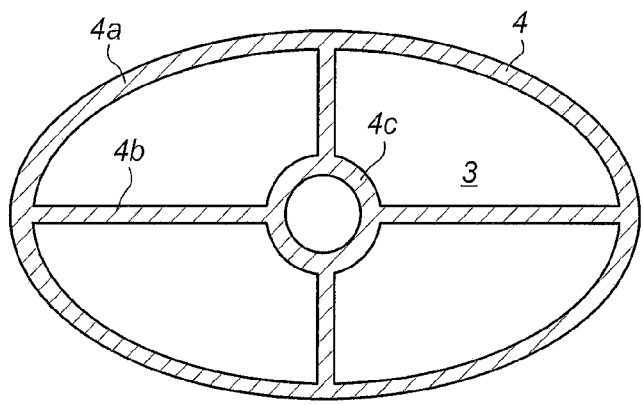
FIG. 1B depicts an embodiment of a membrane support.
Figure 1:
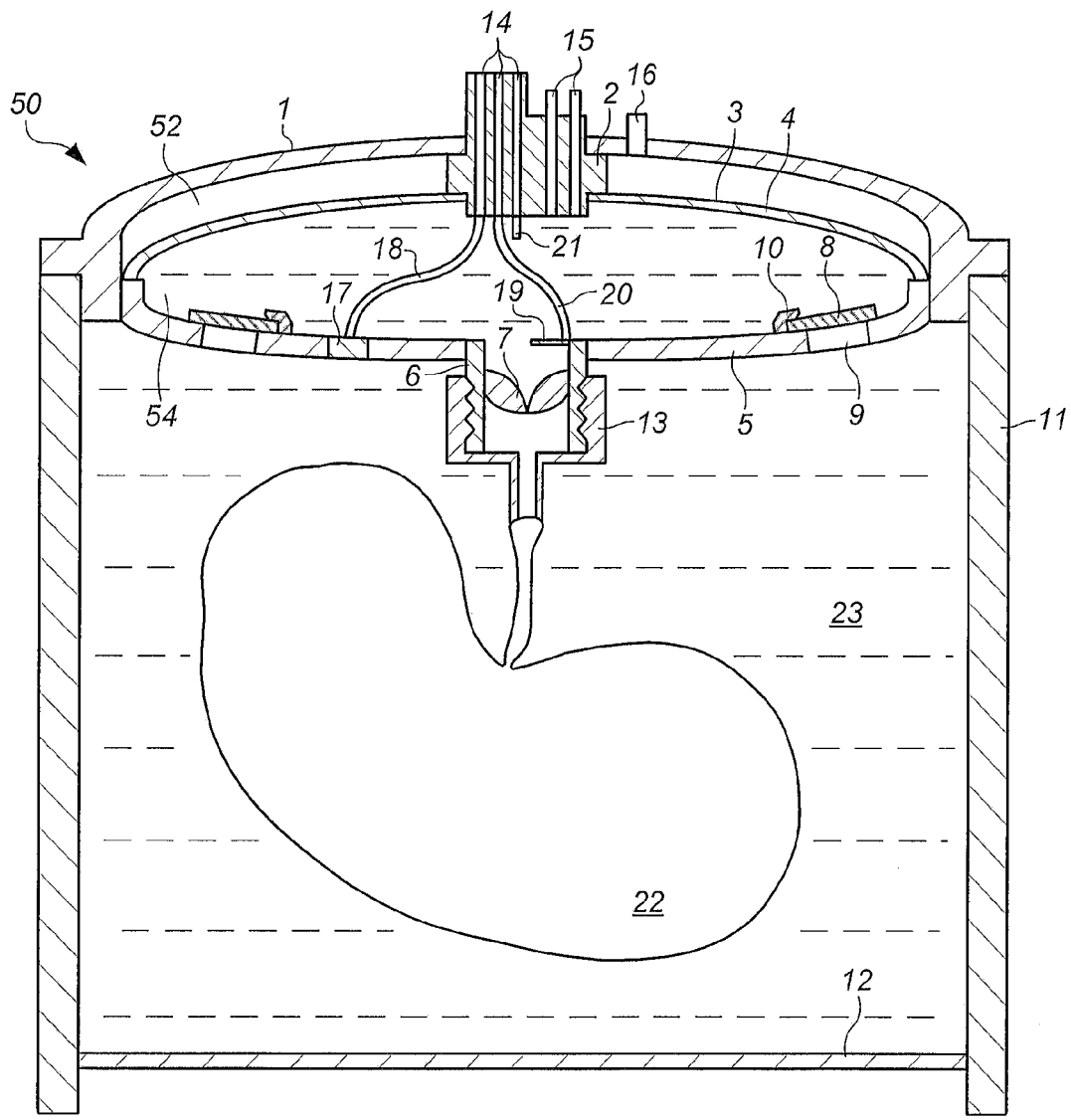
FIG. 1 is a cross-section view of a perfusion apparatus.

Turning now to the drawings, FIG. 1 is a cross-section view of an embodiment of a preservation apparatus for preserving extracorporeal living tissue and organs. The preservation apparatus includes a storage compartment 23 defined by walls 11 and bottom 12. Storage compartment 23 is capable of receiving living tissue and organs 22. The apparatus also includes a cover assembly 50 composed of a lid 1, a support element 5, and a gas permeable membrane 3 disposed between support element 5 and lid 1. When assembled cover assembly 50 together with storage compartment 23 define a storage chamber. Gas permeable membrane 3 in combination with lid 1 defines a pumping chamber 52. In combination with support element 5, gas permeable membrane 3 also defines a perfusion chamber 54.

An oxygen containing gas source is coupled to pumping chamber 52 of the apparatus through port 16. In use, the tissue or organ 22 is submerged in a preservation fluid in the storage compartment 23. The oxygen containing gas is provided at regular intervals into pumping chamber 52, pressurizing the pumping chamber. Oxygen permeates the gas permeable membrane 3 and oxygenates the preservation fluid in perfusion chamber 54. Simultaneously, expansion of the membrane causes perfusion chamber 54 to contract, pumping the oxygenated preservation fluid into the tissue/organ 22. As the oxygenated preservation fluid passes into the tissue/organ, pressure builds up in storage compartment 23. After a predetermined pressure is reached in storage compartment 23, the oxygen flow is stopped. This allows the preservation fluid from the storage compartment 23 to flow through an outlet valve back to perfusion chamber 54, where the dissolved gas, which includes carbon dioxide, is permeated through the gas permeable membrane and removed from pumping chamber 52.

Storage compartment 23, as illustrated in FIG. 1, is elliptical in shape. As used herein an "elliptical" object has the shape of an ellipse. An ellipse is a closed plane curve generated by a point moving in such a way that the sums of its distances from two fixed points are a constant. While the depicted embodiment is in the form of an ellipse other shapes may be used such as a cylindrical shape. Both cylindrical and elliptical storage compartments allow efficient operation during use of the device. The elliptical configuration, however, may better accommodate internal support structures for both donor heart and kidney organs. For example, a long axis dimension of 15 cm and a short axis dimension of 10 cm with a depth of 15 cm appears to provide sufficient lateral distance to the side-walls for adequate motion damping during transport for both hearts and kidneys. These dimensions will also support other organs such as the pancreas and gut. Support of the liver will require larger dimensions and additional configurational requirements. Such changes would be readily apparent to one of ordinary skill in the art.

Storage compartment 23, as illustrated, has rigid sidewalls 11, and an elastic bottom 12. Alternatively, the entire storage compartment may be constructed entirely of an elastic material, such as rubber or plastic. The function of one or more flexible walls is to accommodate increases in fluid pressure during the pumping cycle and is one of the determining factors of the organ flow rate. By design, a wall, for example the bottom, is formed from an elastic material which is capable of deforming to sufficiently to accommodate inflow pulses of the preservation fluid. The flexible wall should have enough elastic recoil so as to return the fluid pulse to the pumping compartment.

Figure 6:
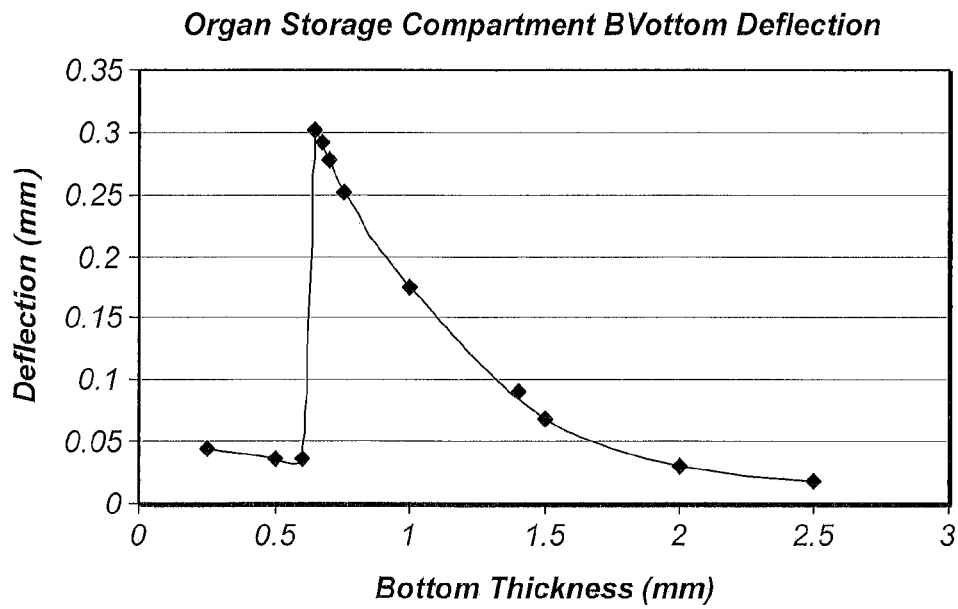
FIG. 6 is a graph depicting the relationship between bottom thickness and deflection of the bottom during pumping.
Figure 7:
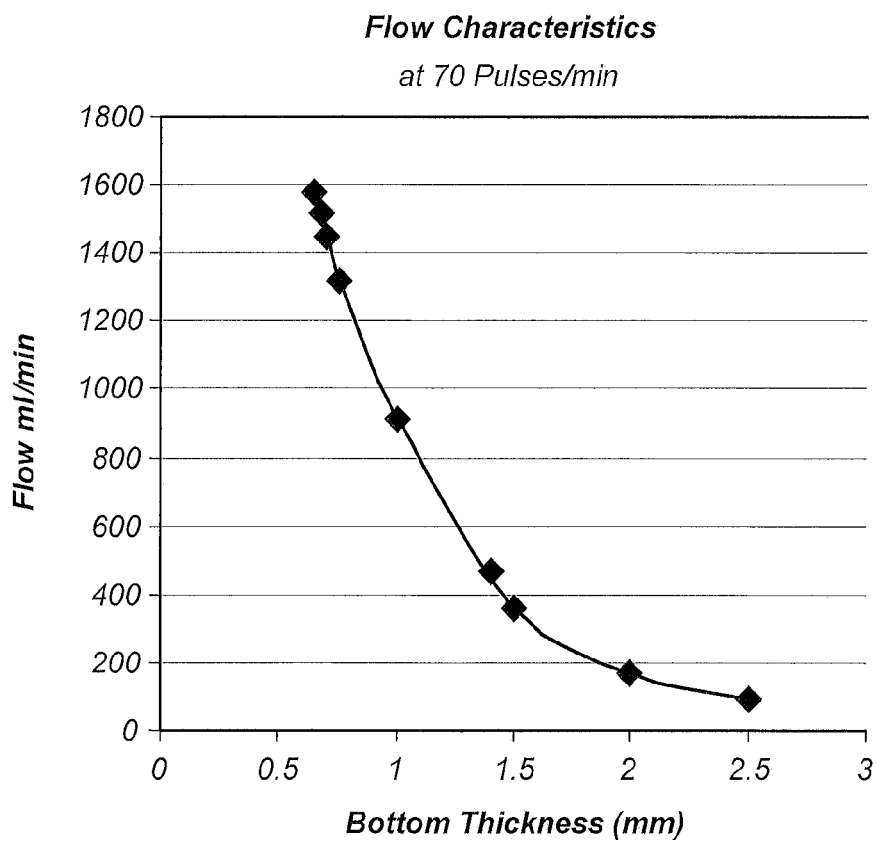
FIG. 7 is a graph depicting the relationship between flow rate and the bottom thickness.

A suitable material for use as a flexible wall for storage compartment 23 may be determined using computer modeling. In one embodiment, a model was created to test a storage compartment having a flexible bottom. In order to evaluate the system as a function of organ storage compartment bottom thickness, a 3D CAD model was evaluated using finite element analysis. Operational parameters were identical to those expected during preservation. Analyses were repeated for bottom thicknesses ranging from 0.065 mm to 2.5 mm. Polycarbonate was chosen as the preferred material. Finite element analysis for the deflection of the bottom with respect to the thickness is depicted in FIG. 6. The analysis shows, for a polycarbonate material, that, at a thicknesses of less than 0.065 mm, the material is expected to fail under the operating load. A bottom thickness of 0.065 mm to 1.25 mm appears to satisfy the design requirements. Finite element analysis of the flow characteristics of a polycarbonate bottom with respect to thickness indicated that a thickness of 1.0 mm provides sufficient elastic recoil to facilitate return flow, without large excursions (see FIG. 7).

Support element 5 is positioned in the apparatus separating storage compartment 23 from perfusion chamber 54. Support element 5 includes inlet port 6 having a one-way inlet valve 7, which is capable of receiving oxygenated perfusate from perfusion chamber 54 and directing its flow into or around the living organ or tissue 22 during the gas input cycle. Support element 5 also includes one or more one-way outlet ports 9 having a one-way valve 8, shown sealed in FIG. 1, which allow unidirectional flow of preservation fluid from storage container 23 to perfusion chamber 54. Outlet valves, in some embodiments, are disk valves that include a disk and an outlet valve disk retainer 10.

In one embodiment, support element 5 has a non-planar bottom surface which contacts the preservation fluid in storage container 23 when the cover assembly 50 is coupled to the storage container. As used herein the term "planar" refers to a characteristic of a surface in which the points of the surface have a curvature of about zero. The term "non-planar" refers to a characteristic of a surface in which portions of the surface have a curvature that is not zero. As used herein the phrase "at least a portion of the surface is substantially non-planar" refers to a surface wherein a portion of the surface is characterized by having a curvature that is not zero. It should be understood that a surface where at least a portion of the surface is substantially non-planar may include portions that are planar (i.e., have a curvature of zero). It should be also understood that an angled surface would also be considered a non-planar surface since the point of intersection of the two planar surface has a curvature that is not zero. In some embodiment, the bottom surface of support element 5 is at least partially arcuate. Bottom surface of support element 5 may form an arc between opposing sides of the storage compartment when the cover assembly engages the storage compartment. When engaged with storage compartment, the bottom surface of support element 5 is at least partially convex with respect to the storage container. In an embodiment, the majority of the bottom surface of support element 5 is curved, arcuate, or convex with respect to the storage container.

While at least a portion of the bottom surface of support element 5 is non-planar, it should be understood that the opposing side, or the upper surface, may be planar or non-planar (as depicted in FIG. 1). The non-planar surface of support element 5 functions to expel air from the organ storage compartment during assembly. Removal of air is important because trapped air or bubbles can get into the preservation fluid and, if pumped into an organ, can cause damage to the organ.

Support element 5 is shaped to conform to the shape of storage compartment 23. When positioned onto the lip of the storage compartment 23, support element 5 defines a closed storage chamber in which the organ or tissue are sealed. In one embodiment, support element 5 is an elliptical concave plate (viewed from above) having a centrally located inlet port 6. The inlet port 6 extends outward and is threaded to allow a quick attachment of the organ or tissue to a connector 13 used to couple the organ or tissue to inlet port 6. Mounting inlet port 6 and organ connector 13 in the center region of support element 5 generally allows the organ to be suspended in the preservation fluid, which offers a number of advantages over prior systems of mounting. For example, this positioning of the inlet port and connector in the center region of support element 5: a. minimizes stress at the organ vascular attachment point; b. minimizes abrasion injury resulting from contact with sidewalls or bottom; c. allows for circumferential immersion of the organ with the oxygenated perfusate; and d. utilizes the circumferential immersion to dampen motion, thus protecting against impact shock.

Inlet port 6 includes a unidirectional inlet valve 7. Inlet valve is configured to inhibit flow of preservation fluid from organ or tissue 22 to perfusion chamber 54. In one embodiment, inlet valve 7 is a tricuspid valve. An embodiment of a tricuspid valve is depicted in FIG. 1A.

The use of a tricuspid valve distorts the perfusate flow to a lesser extent than other valve configurations allowing a more uniform distribution of preservation fluid to the organ arterial supply vessels. This is particularly important in heart preservation since the coronary ostia are located at the root of the aortic arch.

Connector 13 couples organ or tissue to inlet port 6. A variety of connector sizes are provided so as to fit a range of arterial supply vessels of harvested organs and tissues.

A gas permeable membrane 3 is positioned between lid 1 and support element 5. In one embodiment, gas permeable membrane is coupled to a membrane support 4. In an embodiment of a membrane support 4, the membrane support includes an outer coupling member and one or more membrane support elements extending from the outer coupling member toward an interior region of the membrane support. A specific example of such a membrane support 4 is depicted in FIG., 1B. Coupling member 4a forms an outer edge of membrane support 4 and may be used to couple the membrane support to components of the cover assembly (such as lid 1 or support element 5). One or more membrane support elements 4b extend from coupling member 4a toward the interior of membrane support 3. In one embodiment, two or more membrane support elements 4b are coupled to each other in the interior region of membrane support 4. The two or more membrane support elements may be connected to the membrane. As depicted in FIG. 4b, membrane support members are centrally bisecting in the long and short axis and may be coupled to each other through a central member 4c. Alternatively, the individual membrane support members may be coupled directly to each other.

Membrane support 4 is shaped to conform to the shape of storage compartment 23. In one embodiment, membrane support 4 is an elliptical and convex when viewing from above. The convex curvature (as viewed from above) of membrane support 4, with the addition of circumferential and cross membrane support elements, provides rigidity and form to the gas permeable membrane. In an embodiment, a majority of the membrane support is curved, arcuate, or convex with respect to the storage container. This allows the gas permeable membrane to be maintained at an adequate distance from the underside of the lid, such that contact of the gas permeable membrane with the lid is inhibited. Additionally, this design feature also inhibits the membrane from large excursions toward support member 5 thus inhibiting contact of the membrane with the support element 5. Restricting movement of gas permeable membrane 3 with respect to support element 5 and lid 3 minimizes the danger of occlusion of outflow ports 9 during the pressurization phase of the pumping cycle and gas input/vent port 16 during the depressurization phase of the pumping cycle. This use of membrane support 4, therefore, significantly improves perfusate flow, oxygenation of the perfusate, and reduces gas permeable membrane 3 contact with the support element and the lid. The non-planar shape of the membrane support 4 further allows convenient priming of pumping chamber 52.

In the embodiment depicted in FIG. 1b central member 4c provides an opening to receive sensor housing 2. In an embodiment, a sensor housing 2 may be fitted into central member 4c as depicted in FIG. 1. Sensor housing 2 may include data ports 14 and priming ports 15. Sensor housing may also serve as a support to offset the membrane support from lid 1. When membrane support 4 is placed onto the lip of the support element 5, the membrane support and support element 5 define perfusion chamber 54. Priming ports 15 may be used to fill perfusion chamber 54 with preservation fluid such that the pumping chamber 52 is bypassed. Perfusion chamber 54 is filled with preservation fluid through priming ports 15 prior to initiation of the pumping sequence.

Gas permeable membrane 3 is coupled to membrane support 4. In some embodiments, gas permeable membrane 3 is formed from a material that is oxygen permeable; carbon dioxide permeable, has a porosity sufficient to prevent diffusion of waster in its liquid phase through the membrane, has an elasticity with a minimum elongation at break of 30% and a minimum burst strength of 10 psi, and is biocompatible. Oxygen permeability should be in the range of between about 1 ml $O_2$/min/cm$^2$ to 5 ml $O_2$/min/cm$^2$ at 4 C. Carbon dioxide permeability should be in the range of between about 5 ml $CO_2$/min/cm$^2$ to 50 ml $CO_2$/min/cm$^2$ at 4 C. Suitable materials that may be used for a gas permeable membrane include, but are not limited to: silicone rubber, polydimethylsiloxane (PDMS), polytetrafluoroethylene (PTFE), and dimethyl and methylvinyl siloxane copolymers (both unsupported and supported on polyester or the like fibers). Suitable membranes formed from these materials have a thickness ranging from 0.01 mm to 1.0 mm. Examples of commercially available membrane-like materials that may be used include Silon-IPN® (available from Bio Med Sciences, Inc., Allentown, Pa.), True Membrane® (available from Avcore, Inc. of Plymouth, Minn.), and the Silastic® membrane (available from Dow Corning of Midland, Mich.)

In one embodiment, a Silon-IPN® gas permeable membrane has an oxygen permeability at 4 C of about 3.5 ml $O_2$/min/cm$^2$ and a carbon dioxide permeability at 4 C of about 21 ml $CO_2$/min/cm$^2$. The suitability of the membrane was tested with respect to a kidney. At 5 C, a human kidney will consume approximately 0.48 ml $O_2$/min. With an oxygen permeability of 3.5 ml $O_2$/min/cm$^2$ and a membrane area of 120 cm$^2$ a total of 420 ml $O_2$/min can be potentially delivered to the organ during preservation. In order to achieve this level of oxygenation, a minimum partial pressure gradient of oxygen must be maintained during preservation. The membrane area in the preservation device is 120 cm$^2$ and has a thickness of 0.0038 cm. Using the Fick diffusion equation the minimum partial pressure gradient of oxygen needed across the Silon-IPN membrane needed to provide $O_2$ during preservation is given by:

$$0.48 \, ml \, O_2/min = \frac{6.40 \times 10^{-7} ml\,cm}{min\,cm^2 \, mmHg} \frac{120 \, cm^2}{0.0038 \, cm} \Delta pO_2 \, min$$

$$\Delta pO_2 \, min = 23.75 \, mmHg$$

At 5° C., a human kidney will produce 0.384 ml $CO_2$/min. With a carbon dioxide permeability of 21.0 ml $CO_2$/min/cm$_2$ and a membrane area of 120 cm$_2$ a total of 2,520 ml $CO_2$/min can be potentially removed from the organ during preservation. In order to achieve this level of carbon dioxide removal, a minimum partial pressure gradient of carbon dioxide must be maintained during preservation. Similarly, the minimum partial pressure gradient of carbon dioxide needed across the Silon-IPN membrane for removal of $CO_2$ produced during preservation is given by;

$$0.384 \, ml \, CO_2/min = \frac{3.83 \times 10^{-6} ml\,cm}{min\,cm^2 \, mmHg} \frac{120 \, cm^2}{0.0038 \, cm} \Delta pCO_2 \, min$$

$$\Delta pCO_2 \, min = 3.14 \, mmHg$$

These data show that the configuration of the organ preservation device should easily accommodate the metabolic needs of organs such as the heart, which require greater levels of oxygen during preservation than kidneys.

The preservation apparatus is sealed with lid 1. Lid 1 is shaped to conform to the shape of storage compartment 23. In one embodiment, lid 1 is elliptical and convex when viewing from above. When positioned onto the storage compartment 23, lid 1 hermetically seals the preservation apparatus from the surrounding atmosphere. When assembled with membrane support 3, lid 1 and the membrane support define pumping chamber 52. An oxygen containing gas supply source is coupled to lid 1 at gas input/venting port 16. Oxygen containing gas enters into pumping chamber 52 through gas input/venting port 16 during the pumping cycle. Instrumentation ports 14 and priming ports 15 may be coupled to lid 1. Priming ports may be used to pass preservation fluid through lid 1 and membrane support 4 to perfusion chamber 54. Instrumentation ports may allow sensor data lines to be passed through the lid to various sensors disposed within the preservation apparatus.

A variety of internal sensors may be disposed in the preservation apparatus for monitoring the status of the organ or tissue, as well as the storage conditions. In one embodiment, a temperature sensor 21 may be disposed in the perfusion temperature to monitor the temperature of the preservation fluid. Since the preservation fluid is being circulated between perfusion chamber 54 and storage compartment 23 during each pumping cycle, the temperature measured in the perfusion chamber is indicative of the temperature of the fluid in which the organ or tissue is being stored. In an embodiment, a pressure sensor 17 may be disposed in support element 5. Pressure sensor may be coupled to a controller 56 by pressure sensor data conductor 18. Pressure sensor 18 is configured to determine the pressure in storage compartment 23 and perfusion chamber 54. In some embodiments, pressure sensor 17 is a differential pressure sensor capable of measuring the difference in pressure between perfusion chamber 54 and storage compartment 23. Another sensor that may be present is flow sensor 19. Flow sensor 19 may be coupled to inlet port 6 to allow the flow rate of the preservation fluid through the inlet port to be monitored. Flow sensor 19 may be coupled to a controller 56 by a flow sensor data conductor 20. Other sensors, such as a sensor for measuring pumping chamber pressure may be included.

Figure 5:
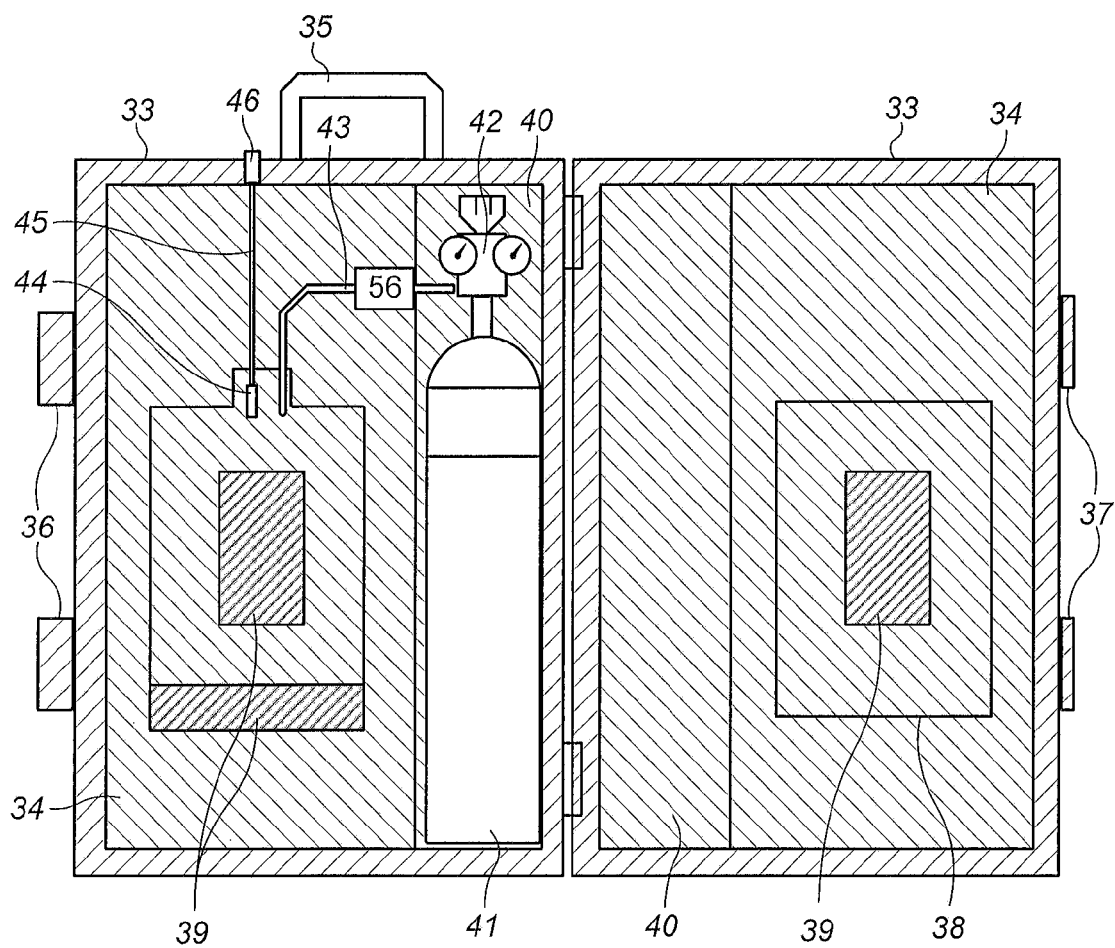
FIG. 5 depicts a storage case for the preservation apparatus in an open configuration.

Controller 56 for controlling the flow of an oxygen containing gas may be attached directly to lid 1, attached directly to the oxygen containing gas supply source or coupled to a conduit running between the oxygen containing gas supply source and lid 1 (See FIG. 5). The configuration where the controller was attached directly to the oxygen containing gas supply source with conveyance and venting of gas via small bore tubing was shown to be equally effective to the other configurations. Attaching or coupling the controller to the oxygen containing gas source, rather than the lid, however, has the advantage of fewer manufacturing steps, lower cost and the potential of re-usability for the controller.

Figure 4A:
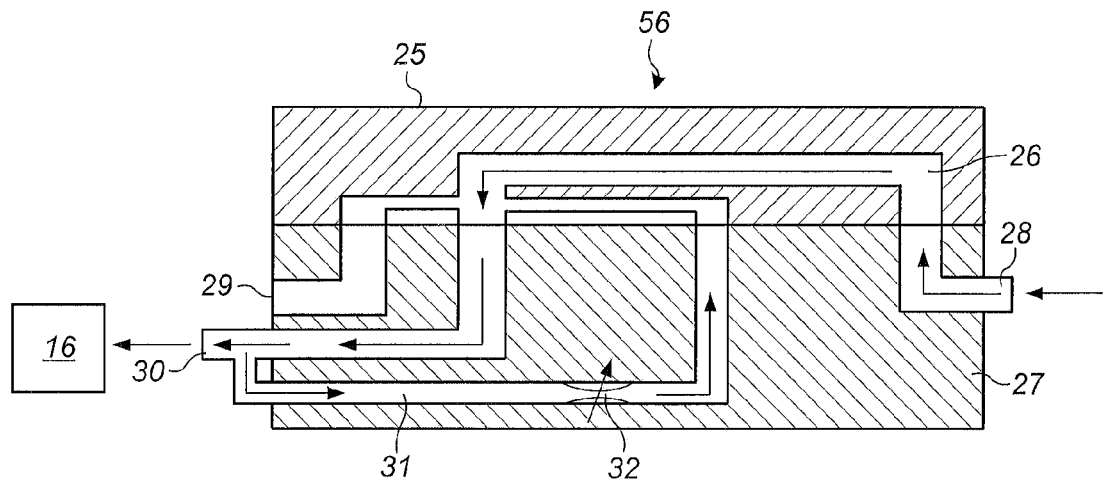
FIG. 4A depicts a schematic diagram of a flow controller during delivery of an oxygen containing gas.
Figure 4B:
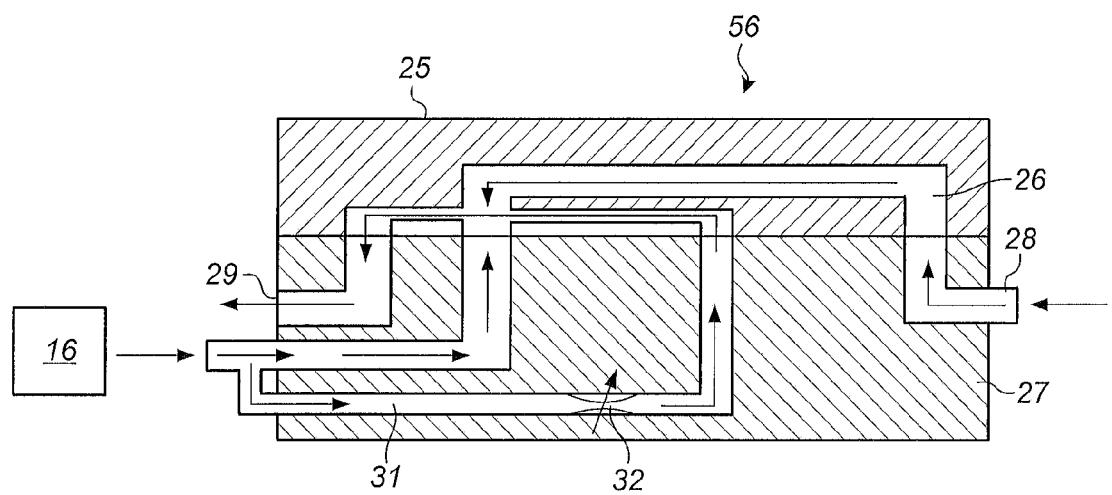
FIG. 4B depicts a schematic diagram of a flow controller during venting of a preservation apparatus.

A schematic drawing of an embodiment of a controller 56 is depicted in FIGS. 4A and 4B. In one embodiment, controller 56 may be a microfluidics controller configured as an exclusive OR logic gate. FIG. 4A illustrates the operation of an exclusive OR microfluidics controller having an exclusive OR gate 25 coupled to a flow control manifold. During the gas input cycle, properly proportioned gas from compressed gas cylinders enters gas inlet port 28, and flows as shown through channels 26 to lid port 16 via outlet 30 to pressurize pumping chamber 52. Feedback circuit 31 simultaneously experiences flow. When the flow in feedback circuit 31 exceeds the flow through outlet 30, supply flow switches back to gas exhaust port 29, as shown in FIG. 4B. When the volume of gas from the previous pressurization cycle is vented, exhaust flow to gas exhaust port 29 falls to zero, and the supply flow then switches to provide flow to outlet 31, repeating the cycle. The pressure of the oxygen containing gas supplied to the pumping chamber 52 may be controlled using pressure control regulator 32. Controller 56 is configured to have an operational requirement of about 1 to 2 psi and a minimum flow requirement of about 0.75 liters/min.

Cover assembly 50 may be assembled prior to use of the preservation apparatus. To assemble the cover assembly, gas permeable membrane 3 is bonded to membrane support 4 using a silicone sealant or other appropriate sealant. Membrane support 4, with gas permeable membrane 3 coupled to the support, is inserted into the lid and permanently sealed into position with a similarly appropriate sealant. The slightly different radii of curvature of membrane support 4 and lid 1 naturally creates a space that will function as pumping chamber 52. The support element 5 is inserted into lid 1 and sealed into position with a similarly appropriate sealant. Membrane support 4 together with the support element 5 naturally form a perfusion chamber 54 in which preservation fluid is enriched with oxygen, and carbon dioxide is removed. When assembled these elements combine to form cover assembly 50.

Donor organ or tissue 22 is attached to inlet port 6 on support element 5 and cover assembly 50 is seated onto the rim of storage container 23, previously filled with preservation fluid. Lid 1 may be threaded for attachment of cover assembly to storage compartment 23. Other methods of forming a seal between cover assembly 50 and storage compartment 23 may be used such as latches, straps, clamps, snap caps, friction fit or other methods that meet the criterion of providing a snug, hermetically sealed connection between the individual compartments. When assembled, cover assembly 50 forms a hermetically sealed unit with storage compartment 23, which may be operated in any physical orientation with appropriate adjustments to the gas pressure injected into pumping compartment 52. Preservation fluid is maintained at a constant level in the preservation apparatus by gas permeable membrane 3, which is sealingly positioned over the preservation fluid in perfusion compartment 54 by membrane support 4 and lid 1.

Perfusion chamber 54, between membrane support 4 and support element 5 is primed with preservation fluid via priming ports 15 located in lid 1. In use, one priming port is used to introduce the preservation fluid into perfusion chamber 54. The other priming port serves as a gas outlet for releasing gas from perfusion chamber 54 as the chamber is filled with preservation fluid.

Figure 2:
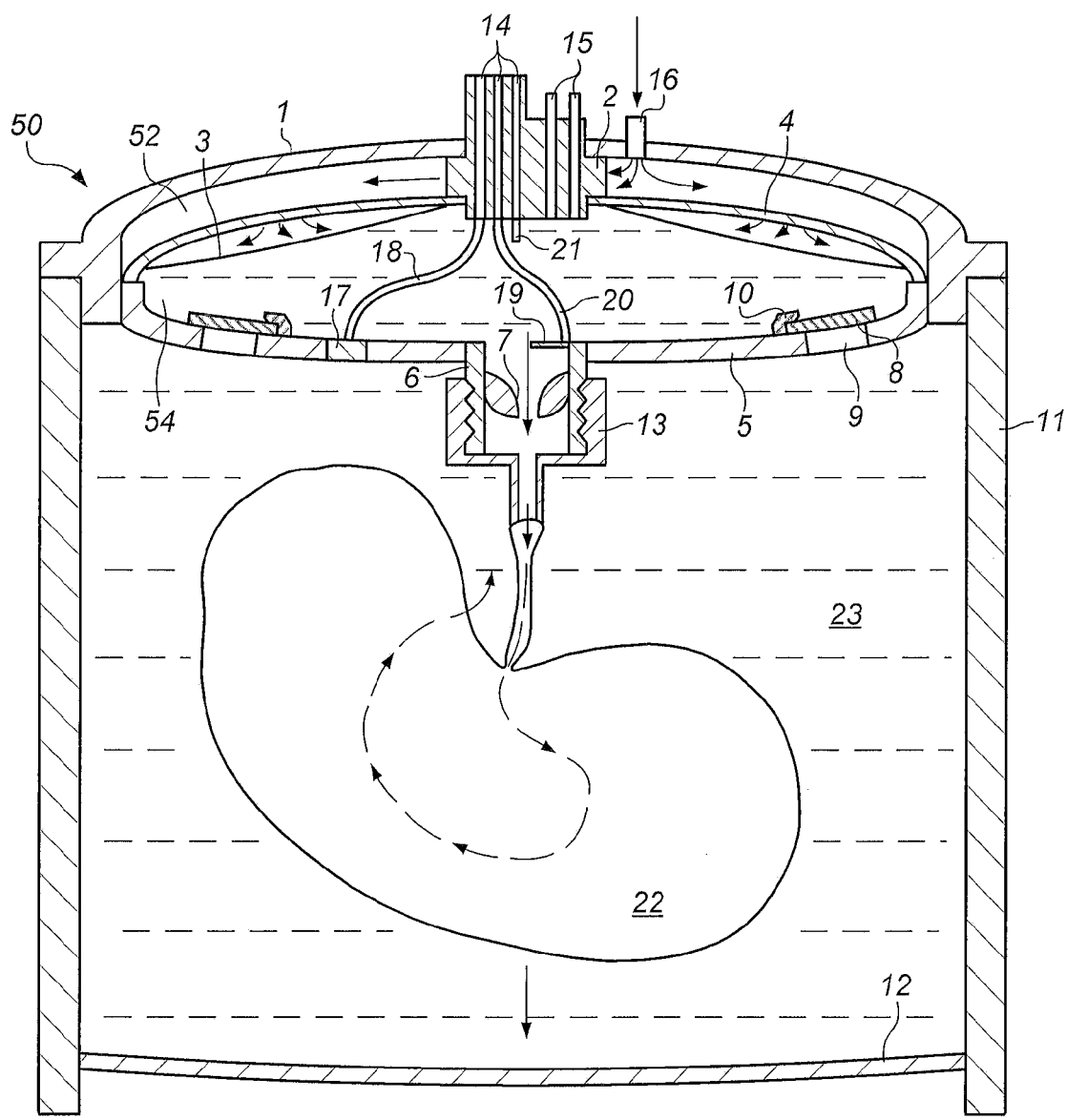
FIG. 2 is a cross-section view of a perfusion apparatus during pressurization.

During oxygenation, shown in FIG. 2, controller 56 (not shown) allows the flow of an oxygen containing gas into pumping chamber 52. The increased oxygen concentration in pumping chamber 52 causes gas to permeate gas permeable membrane 3 and oxygenate preservation fluid in perfusion chamber 54. Simultaneously, the difference in pressure expands gas permeable membrane 3, which forces oxygenated preservation fluid from perfusion chamber 54 into inlet port 6 and through inlet valve 7 into organ or tissue 22. The pressure of the preservation fluid in perfusion chamber 54 keeps outlet valves 8 shut so that flow of fluid through outlet ports 9 is inhibited. Membrane support 4, limits the amount of movement of gas permeable membrane 3, such that the membrane is inhibited from being pushed against inlet port 6. Flexible compliant bottom 12 of chamber 23 expands, as shown in FIG. 2, to accommodate the increased compartment volume caused by introduction of oxygenated preservation fluid into living organ or tissue 22 and storage compartment 23.

Preservation fluid may be the University of Wisconsin Solution with HES or PEG, as referenced in Wicomb et al., 48, Transplantation 6-9 (1989) and Wicomb et al. 49 Transplantation 261-64 (1990), the disclosures of which are incorporated herein by reference. Other general categories of acceptable perfusion/storage media compatible with the present invention include the perfusion/storage media described in the following references, disclosures of which are each expressly incorporated herein by reference: Modified Krebs-Henseleit Solution, as referenced in Petsikas et al., 9 J. Heart Transplantation 543-547 (1990); Bretschneider HTK Solution, as referenced in Minten et al., 10 J. Heart and Lung Transplantation 71-78 (1991); Wicomb Solution, as referenced in Wicomb et al., 21 Transplantation Proceedings 1366-68 (1989); Tyers' Solution, as referenced in Qayumi et al., 4 J. Investigative Surgery 93-102 (1991); and preservation fluids referenced in U.S. Pat. Nos. 5,149,321, 5,234,405, and 5,395,314. Other preservation fluids not explicitly listed herein may be used if they are compatible with components of the preservation device.

Figure 3:
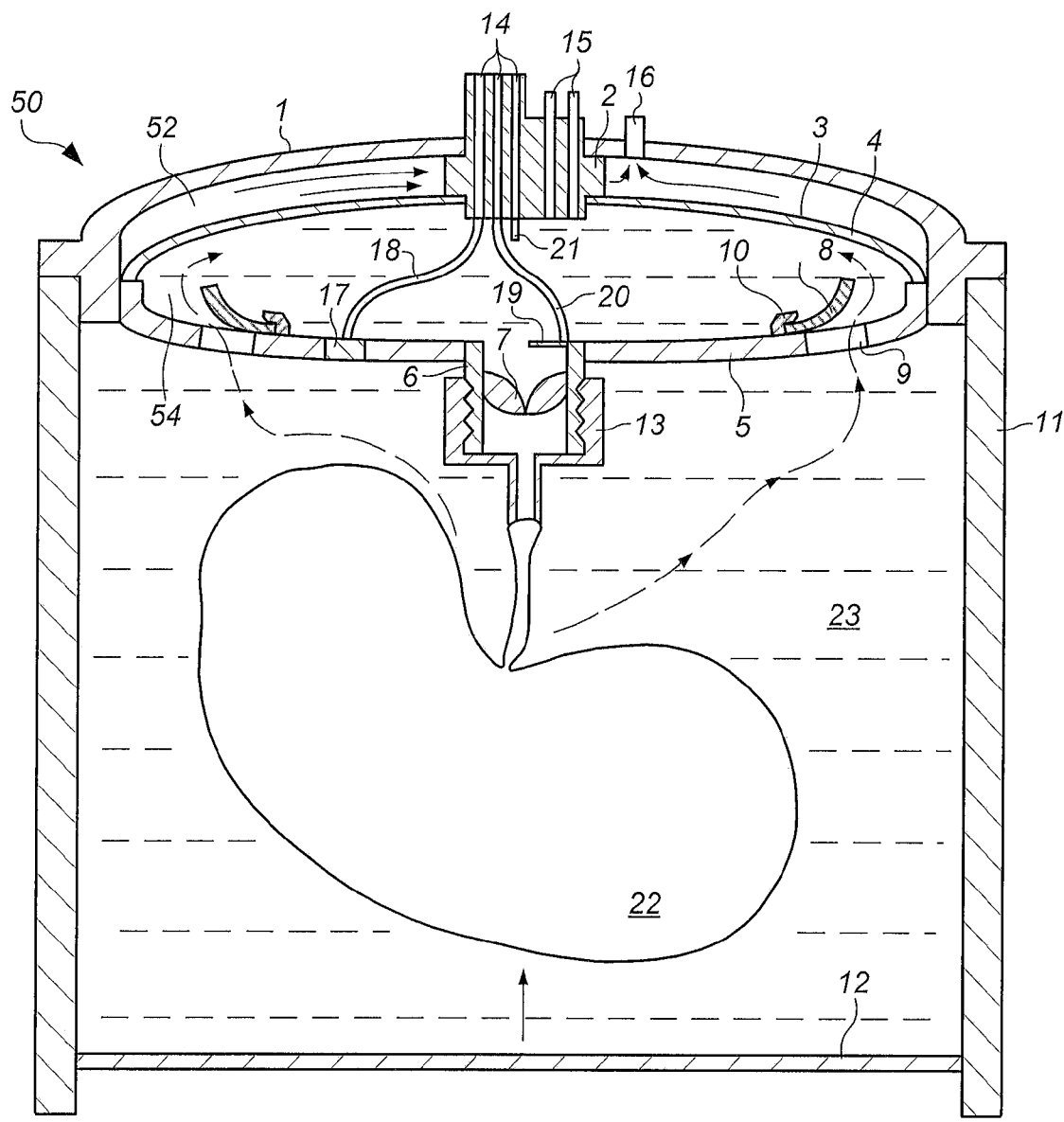
FIG. 3 is a cross-section view of a perfusion apparatus during venting.

FIG. 3 illustrates the preservation apparatus of FIG. 1 during the gas exhaust cycle. When the entry of the gas into pumping chamber 52 ceases, the pressure is relieved, relaxing gas permeable membrane 3. In response to the drop in pressure, inlet valve 7 closes establishing a pressure differential between storage chamber 3 and perfusion chamber 54. The pressure from storage chamber 23 causes outlet valves 8 to open to allow preservation fluid to flow from storage compartment 23 into perfusion chamber 54. In the perfusion chamber 54, gas from the preservation fluid, which now has a concentration of carbon dioxide expelled from organ or tissue 22, permeates gas permeable membrane 3 into pumping chamber 52, where it is expelled through lid port 16 and in turn through gas exhaust port 29 of the controller.

Figure 8:
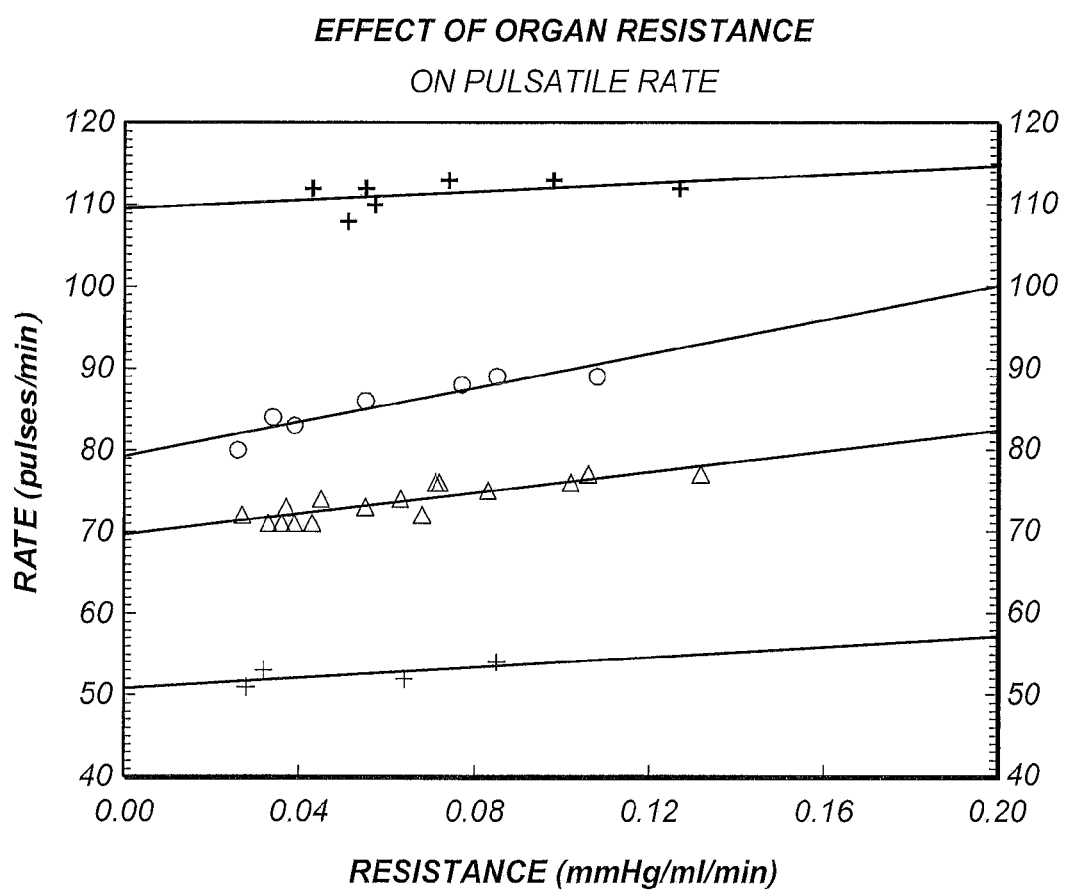
FIG. 8 is a graph depicting the relationship between organ resistance on pulsatile rate.

The operation of preservation apparatus may be modeled to test the operating parameters of the system. In a simulated model, shown in FIG. 8, increasing the simulated organ resistance increased the operating frequency of the fluidics actuator by 11.3±7.1 pulses/min. All operating frequencies exhibited similar increases. The systolic and diastolic pressures in the perfusion chamber and the storage compartment were similar and ranged between 20 and 23 mmHg/10-12 mmHg. The perfusion chamber pressure profile exhibited a more rapid rise in early systole as compared to the storage compartment pressure. The preservation fluid flow at each frequency tested exhibited similar profiles. Pulse flow at 100 pulses/min averaged slightly more than 4 ml. Pulse duration varied between 0.5 and 0.75 sec.

Figure 9:
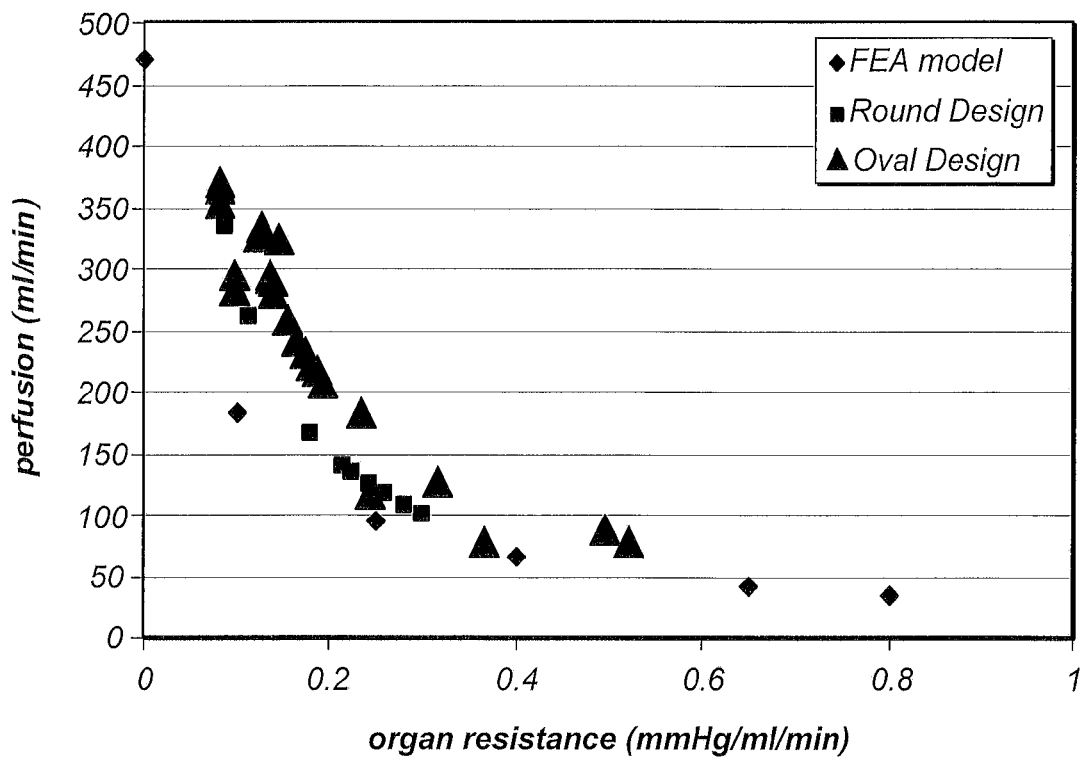
FIG. 9 is a graph depicting organ perfusion as a function of organ resistance.
Figure 10:
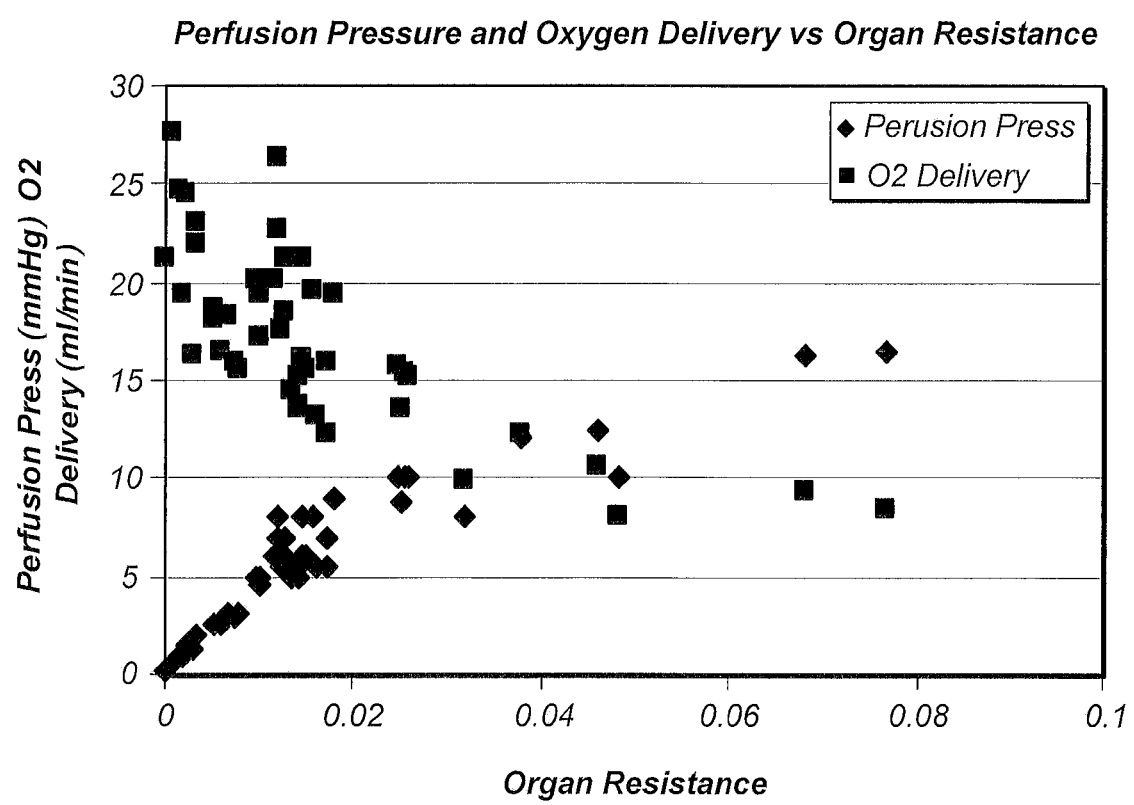
FIG. 10 is a graph depicting perfusion pressure and oxygen delivery vs. organ resistance.

Maximum flow for the system with no organ resistance load was in excess of 450 ml/min. As organ resistance was increased, preservation fluid (perfusion) flow rapidly declined to a plateau of 10 ml/min, as shown in FIG. 9. A comparison of the oval design to the cylindrical design shows no significant variation in operation. Conversely, perfusion chamber pressure rose as simulated organ resistance was increased, as shown in FIG. 10. While the oxygen delivery initially declined rapidly, 12 times the oxygen requirement for a human heart stored at 4 C was available even at the highest resistance level.

Figure 11:
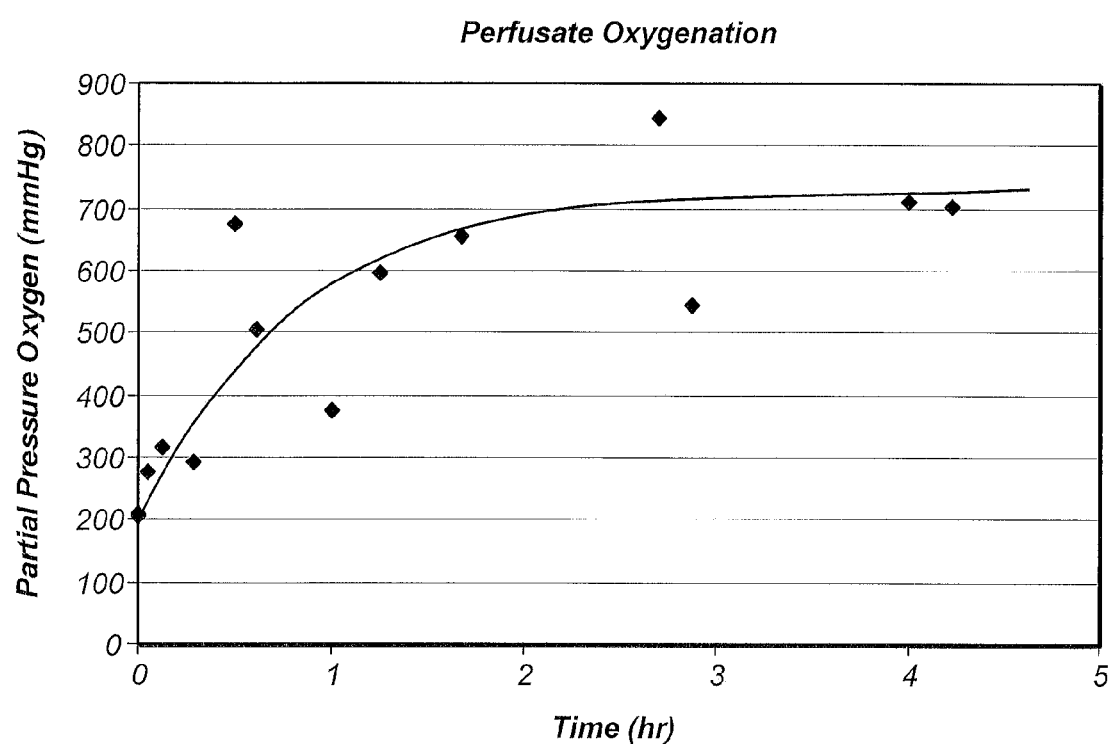
FIG. 11 is a graph depicting the relationship between the partial pressure of oxygen in the preservation fluid over time.

FIG. 11 depicts the rate of oxygenation of the preservation fluid. Oxygenation of the preservation fluid (perfusate) was at a rate of 9.8 mmHg/min. The preservation fluid (perfusate) achieved an oxygen partial pressure of 575 mmHg within the first hour. Full saturation of the preservation fluid (perfusate) with oxygen occurred within 3 hours at a partial pressure in excess of 700 mmHg.

FIG. 5 shows a case 33 for the preservation apparatus in an open configuration. The case is sized to accommodate the organ preservation device in cavity 38, at least one oxygen containing gas supply 41 (e.g., a D size oxygen cylinder) with its gas regulator 42, and cooling blocks 39. In some embodiment, case includes a retractable handle 35 and wheels to provide convenience for transport. In other embodiments, handle 35 is fixed for carrying by hand. The case shell is optimally manufactured from a high density polymer (e.g., polyurethane) to provide resiliency to impact and ease of fabrication. The case may include secure latching mechanisms to insure the case is not inadvertently opened during transport. In an embodiment, case includes hasps 36 which interact with latches 37 to keep the case closed during transport. The external surfaces may be appropriately embossed with logos and disclosures.

Internally, the case will be filled with a material 34 having a high insulative index such as Styrofoam or aerogel insulation. Formed in insulative material 34 is a cavity 38 for accepting the preservation apparatus, cavity 40 for accepting oxygen cylinder 41, and cooling block cavities 39.

The total thermal load ($H_{tot}$) on the transport case during 12 hours of operation is the sum of the heat content of the air inside the capsule storage area ($H_{air}$), the heat content of the capsule and its contents ($H_{cap}$), and the heat infiltration during 12 hours ($H_{infilt}$).

$$(H_{tot}) = (H_{air}) + (H_{cap}) + (H_{infilt})$$

The heat content of the air inside the capsule storage area is given by;

$$(H_{air}) = c_{air}(m_{air}))T$$

Where $c_{air}$ is the specific heat for air, $m_{air}$ is the mass of the air in the capsule storage area,) T is the temperature differential between ambient and storage temperatures (30° C.-5° C.)

$$(H_{air}) = 2.4 \text{ cal/g}° \text{C.}(20.8 \text{ g})25° \text{C.}$$

$$(H_{air}) = 1248 \text{ cal}$$

The capsule and its contents can be considered as contributing no heat load to the system since they will have been reduced to the storage temperature prior to installation into the transport carrier. During harvest, the organ will be purged with cold 4 C preservation fluid, and doused with several liters of similarly cold normal saline. The preservation fluid will also be cold at 4 C. Because the mass of the capsule is small relative to the preservation solution, its heat content will be rapidly absorbed by the preservation solution.

$$(H_{cap}) = 0$$

Heat infiltration during 12 hours of storage is the thermal conductivity of aerogel ($k_{areogel}$)×the surface area of the capsule storage area ($SA_{cap}$)×the temperature differential between inside and outside the transport carrier)T (30° C.-5° C.)/transport carrier wall thickness ($WT_{case}$).

$$(H_{infilt}) = k_{aerogel}(SA_{cap})T/WT_{case}$$

$$(H_{infilt}) = 0.0012 \text{ cal/min cm }° \text{C.}(6750 \text{ cm}^2)25° \text{C./1.5 cm}$$

$$(H_{infilt}) = 135.0 \text{ cal/min}$$

$$(H_{infilt}) = 135.0 \text{ cal/min} \times 60 \text{ min/hr} \times 12 \text{ hrs}$$

$$(H_{infilt}) = 97,200 \text{ cal/12 hrs}$$

The total heat load during 12 hours is therefore;

$$(H_{tot}) = 1,248 \text{ cal} + 0 \text{ cal} + 97,200 \text{ cal}$$

$$(H_{tot}) = 98,448 \text{ cal}$$

In one embodiment, cooling blocks are used to keep the preservation apparatus cool. One embodiment of a cooling device are cooling blocks (e.g., Blue Ice® cold bricks, commercially available from Pelton Sheppard Industries, Stockton, Calif.). The amount of heat a Blue Ice® brick can absorb ($H_{abs}$) is given by the product of the specific heat of the brick ($c_{BL}$), the mass of the brick ($m_{BL}$), and the temperature differential between ambient and storage temperatures T (30 C–5 C)

$$(H_{abs}) = c_{BL} m_{BL})T$$

$$(H_{abs}) = 3.35 \text{ cal/g}° \text{C.} \times 896 \text{ g} \times 25° \text{C.}$$

$$(H_{abs}) = 75,000 \text{ cal}$$

The number of bricks necessary for absorbing the total heat load for 12 hours is;

$$\text{\# bricks} = H_{tot}/H_{abs} = 98,448 \text{ cal/12 hrs}/75,000 \text{ cal} = 1.31$$

Utilization of two Blue Ice® bricks will provide for sufficient maintenance of storage temperature between 4 and 7° C. for 12 hours. Other cold bricks may be used and the number of bricks needed can be determined using similar calculations.

Controller 56 may be positioned in case between oxygen containing gas supply source 41 and preservation apparatus gas input/venting port 16. Conduit 43 may conduct oxygen containing gas from oxygen supply source 41, through controller 56 to the preservation apparatus. Monitoring of the preservation device may be performed using external monitoring device coupled to the preservation apparatus sensors via data cable 45 and external data port 46.

The present invention is not limited to preserving kidneys, as depicted; any living tissue in which the main arterial supply vessel can be isolated and cannulated can potentially be stored in the claimed device. This includes organs such as lungs, kidneys, livers, and pancreas, and extremities such as fingers and toes. In addition, tissue (e.g., corneas) that cannot be perfused but requires precise hypothermic storage can also be maintained within the claimed device.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An apparatus comprising:
a storage compartment, the storage compartment configured to hold an organ or tissue and a preservation fluid; and
a cover assembly configured to engage the storage compartment, the cover assembly comprising:
a support element; wherein the support element together with the storage compartment define a storage chamber;
a lid;
a membrane support positioned between the support element and the lid, the membrane support comprising an outer coupling member and one or more membrane support elements extending from the outer coupling member toward an interior region of the membrane support, wherein the one or more membrane support elements couple to a central member; and
a gas permeable membrane coupled to the membrane support, wherein the gas permeable membrane is coupled to the one or more membrane support elements and the central member such that the membrane is inhibited from moving toward
a center of the cover assembly when filled with a gas;
wherein the membrane support positions the gas permeable membrane between the support element and the lid, and wherein the membrane support elements inhibit contact of the membrane with the lid and the support element.

2. The apparatus of claim 1, wherein the membrane support comprises two or more membrane support elements that are connected to the membrane.

3. The apparatus of claim 1, wherein the membrane support defines an opening configured to receive a sensor housing.

4. The apparatus of claim 1, wherein at least a portion of the membrane support is substantially non-planar.

5. The apparatus of claim 1, wherein the majority of the membrane support is curved, arcuate, or convex with respect to the storage container.

6. The apparatus of claim 1, wherein the membrane support and the lid define a pumping chamber configured to receive oxygen containing gas.

7. The apparatus of claim 1, wherein the membrane support and the support element define a perfusion chamber configured to hold preservation fluid during use.

8. The apparatus of claim 1, wherein the gas permeable membrane inhibits diffusion of water through the membrane.

9. The apparatus of claim 1, wherein the gas permeable membrane allows diffusion of oxygen and carbon dioxide through the membrane.

10. The apparatus of claim 1, wherein the storage compartment has an elliptical shape.

11. The apparatus of claim 1, wherein the storage compartment comprises a wall and a bottom, wherein the wall is composed of a substantially rigid material and wherein the bottom is composed of an elastic material.

12. The apparatus of claim 1, wherein the support element comprises a port configured to engage an organ or tissue, wherein the port is configured to allow unidirectional flow of fluid through the support element to the organ or tissue during use.

13. The apparatus of claim 1, wherein the support element comprises one or more ports configured to allow unidirectional flow of fluid from the storage compartment to the cover assembly during use.

14. The apparatus of claim 1, further comprising a controller connected to the lid, wherein the controller is configured to control the flow of oxygen containing gas to the cover assembly such that:
oxygen containing gas is delivered to the cover assembly when a pressure of the storage compartment is below a predetermined pressure; and
flow of oxygen containing gas is discontinued, and gasses allowed to vent from the cover assembly, when the pressure of the storage compartment is at or above the predetermined pressure.

15. The apparatus of claim 1, further comprising a pressure sensor configured to measure a pressure in the storage compartment.

16. The apparatus of claim 1, further comprising a pressure sensor configured to measure a pressure differential between the storage compartment and the perfusion chamber during use.

17. The apparatus of claim 1, wherein the support element and the gas permeable membrane are connected to the lid.

* * * * *